(12) United States Patent
Tsang et al.

(10) Patent No.: US 9,199,073 B2
(45) Date of Patent: Dec. 1, 2015

(54) NERVE STUMP INTERFACE AND AXONAL REGENERATION SYSTEM FOR GENERATING AN ELECTRIC FIELD FOR PROMOTING AND GUIDING AXONAL REGENERATION

(71) Applicant: Agency for Science, Technology and Research, Singapore (SG)

(72) Inventors: Wei Mong Tsang, Singapore (SG); Tao Sun, Singapore (SG); Minkyu Je, Singapore (SG); Tack Boon Yee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 81 days.

(21) Appl. No.: 14/093,351

(22) Filed: Nov. 29, 2013

(65) Prior Publication Data

US 2014/0148886 A1 May 29, 2014

(30) Foreign Application Priority Data

Nov. 29, 2012 (SG) .................................. 201208821

(51) Int. Cl.
*A61N 1/00* (2006.01)
*A61N 1/05* (2006.01)
*A61B 5/04* (2006.01)
*A61N 1/32* (2006.01)
*A61N 1/36* (2006.01)

(52) U.S. Cl.
CPC ............ *A61N 1/0551* (2013.01); *A61B 5/04001* (2013.01); *A61N 1/326* (2013.01); *A61N 1/36103* (2013.01); *Y10T 29/49002* (2015.01)

(58) Field of Classification Search
CPC ........................... A61N 1/0556; A61N 1/0551
USPC ......................................................... 607/118
See application file for complete search history.

(56) References Cited

U.S. PATENT DOCUMENTS 6,908,470 B2 * 6/2005 Stieglitz et al. ............... 606/118
8,676,334 B2 * 3/2014 Youn et al. ...................... 607/48

* cited by examiner

*Primary Examiner* — Amanda Patton
*Assistant Examiner* — Philip Edwards
(74) *Attorney, Agent, or Firm* — Schwegman Lundberg & Woessner, P.A.

(57) ABSTRACT

The present invention provides a nerve stump interface for generating an electric field for promoting and guiding axonal regeneration and an electric field assisted axonal regeneration system. The nerve stump interface comprises a sieve having a plurality of holes. A strip is coupled to the sieve. A first electrode is provided at one of the plurality of holes and a second electrode is provided on the strip. The strip is arranged to space the second electrode from the first electrode. The first electrode and the second electrode are for generating the electric field. At least one securing element is provided on a side of the strip to allow that side of the strip to affix against an opposite side of the strip. The present invention also provides a method for assembling the electric field assisted axonal regeneration system.

20 Claims, 8 Drawing Sheets

|  | Material | σ [S/m] |
|---|---|---|
| Tube | Silicone | $10^{-16}$ |
| Substrate | Polyimide | $10^{-16}$ |
| Electrode | Gold | $45.6 \times 10^6$ |
| Surrounding | Tissue | 0.1 |

Figure 7

NERVE STUMP INTERFACE AND AXONAL REGENERATION SYSTEM FOR GENERATING AN ELECTRIC FIELD FOR PROMOTING AND GUIDING AXONAL REGENERATION

PRIORITY APPLICATION(S)

The present application claims the benefit of priority under 35 U.S.C. §119 to Singapore Patent Application No. 201208821-7, filed Nov. 29, 2012, which is hereby incorporated by reference in its entirety.

FIELD OF INVENTION

The invention relates generally to a nerve stump interface and axonal regeneration system by generating an electric field for promoting and guiding axonal regeneration.

BACKGROUND

An electrode interface, that has high selectivity and is reliable, at proximal peripheral nerve stumps is desirable for amputees and patients with peripheral nerve injury. For example, the peripheral signal recorded from the amputees and patients can be used to control an artificial limb. Alternatively, the ability to record a neural signal from the proximal nerve stump and to actuate target muscle fibres via a wireless link shows an opportunity to bypass reliance on the natural ability of the nerve to regenerate and to restore limb movement of patients with peripheral nerve injury.

Regenerative electrodes show potential for high selectivity and reliable peripheral nerve interfaces (PNI). An example is a sieve electrode which can be fabricated from silicon (Si), polymer and epoxy. The sieve electrode is placed between two cut ends of a nerve trunk and some of the sieve electrode holes are constructed with ring electrodes. After the nerve fibres regenerate through the holes, an intimate electrical contact can be formed, thus allowing both reliable recording of neural signals and efficient stimulation on the residual nerve fibers.

However, applicability of sieve electrodes is critically dependent on the success of axonal regeneration through the holes with an electrode and the time taken for axonal regeneration. For amputees (who suffer loss of the distal nerve stump) or when separation between the proximal nerve stump and the distal nerve stump in a patient is too far way for axonal regeneration, the proximal nerve stump needs to be surgically reinnervated into other spare muscles. This could result in painful neuromas. For such circumstances, polyimide based sieve-like electrodes have been proposed. The device has a fixation flap structure and integrated biological cells. The device may be adapted for use with a distal nerve stump without a guidance tube, but it cannot be adapted for use with a proximal nerve stump.

Various other methods, including chemical and topographic methods, have been proposed to guide and promote axonal regeneration. For instance, a regenerative electrode design has been proposed containing multiple microfluidic channels that serve as a guidance tube for nerve regeneration and as fluidic pathways for injecting chemicals such as nerve growth factors (NGF) to promote nerve growth. Alternatively, an electrode design with micro-channels structure having embedded biodegradable polymer has been proposed. The drugs for promoting and guiding nerve regeneration are incorporated into the polymer and released into the body during the polymer degradation. However, both of these designs introduce additional massive micro-channel structures, which can trigger an extra tissue response when compared to the standard sieve electrode. Further, delivering drugs through microfluidic channels requires an external pump system and the dosage of drugs is constrained in the biodegradable polymer approach.

Research has gone into creating various topographic structures to direct regenerating axons though electrode holes, but the topographic structures introduce an additional massive-structure into the standard sieve electrode. Finally, research effort has been put into the modification of guidance tubes (or conduits) to promote and guide nerve regeneration. However, these approaches can only guide the nerve growth through the guidance tube rather than guide the nerve growth through the sieve holes with an electrode.

There is thus a need to address the above drawbacks relating to interfaces that promote axonal regeneration.

SUMMARY

According to one aspect of the invention, there is provided a nerve stump interface for generating an electric field for promoting and guiding axonal regeneration, the nerve stump interface comprising a sieve comprising a plurality of holes; a strip coupled to the sieve; a first electrode provided at one of the plurality of holes and a second electrode provided on the strip, the strip being arranged to space the second electrode from the first electrode, the first electrode and the second electrode for generating the electric field; and at least one securing element provided on a side of the strip to allow that side of the strip to affix against an opposite side of the strip.

According to another aspect of the invention, there is provided an electric field assisted axonal regeneration system comprising a guidance tube with an open end; a sieve comprising a plurality of holes, the sieve disposed in a perpendicular orientation within the guidance tube, so that the plurality of holes faces the open end of the guidance tube; a strip coupled to the sieve and rolled to form a generally ring shaped structure, the ring shaped structure having an orientation that is generally parallel to the sieve; a first electrode provided at one of the plurality of holes; and a second electrode provided on the strip, the strip being arranged to space the second electrode from the first electrode, the first electrode and the second electrode for generating the electric field.

According to a third aspect of the invention, there is provided a method for assembling an electric field assisted axonal regeneration system, the method comprising: providing a nerve stump interface comprising a sieve comprising a plurality of holes; a strip coupled to the sieve; a first electrode provided at one of the plurality of holes and a second electrode provided on the strip, the strip being arranged to space the second electrode from the first electrode, the first electrode and the second electrode for generating the electric field; and a securing element provided in the vicinity of each opposite end of the strip; rolling the strip to form a ring shaped structure by having the securing element at each opposite end engage one another; immobilizing the ring shaped structure; removing excess from the opposite ends of the strip that extend from the engaged securing elements; folding either the ring shaped structure or the sieve to be parallel to each other; and inserting the ring shaped structure within a guidance tube.

BRIEF DESCRIPTION OF THE DRAWINGS

Example embodiments of the invention will be better understood and readily apparent to one of ordinary skill in the art from the following written description, by way of example only, and in conjunction with the drawings. The drawings are not necessarily to scale, emphasis instead generally being placed upon illustrating the principles of the invention, in which:

FIG. 7 shows a table of possible materials that can be used for the various components of the electric field assisted axonal regeneration system shown in FIG. 3.

DEFINITIONS

Figure 1:
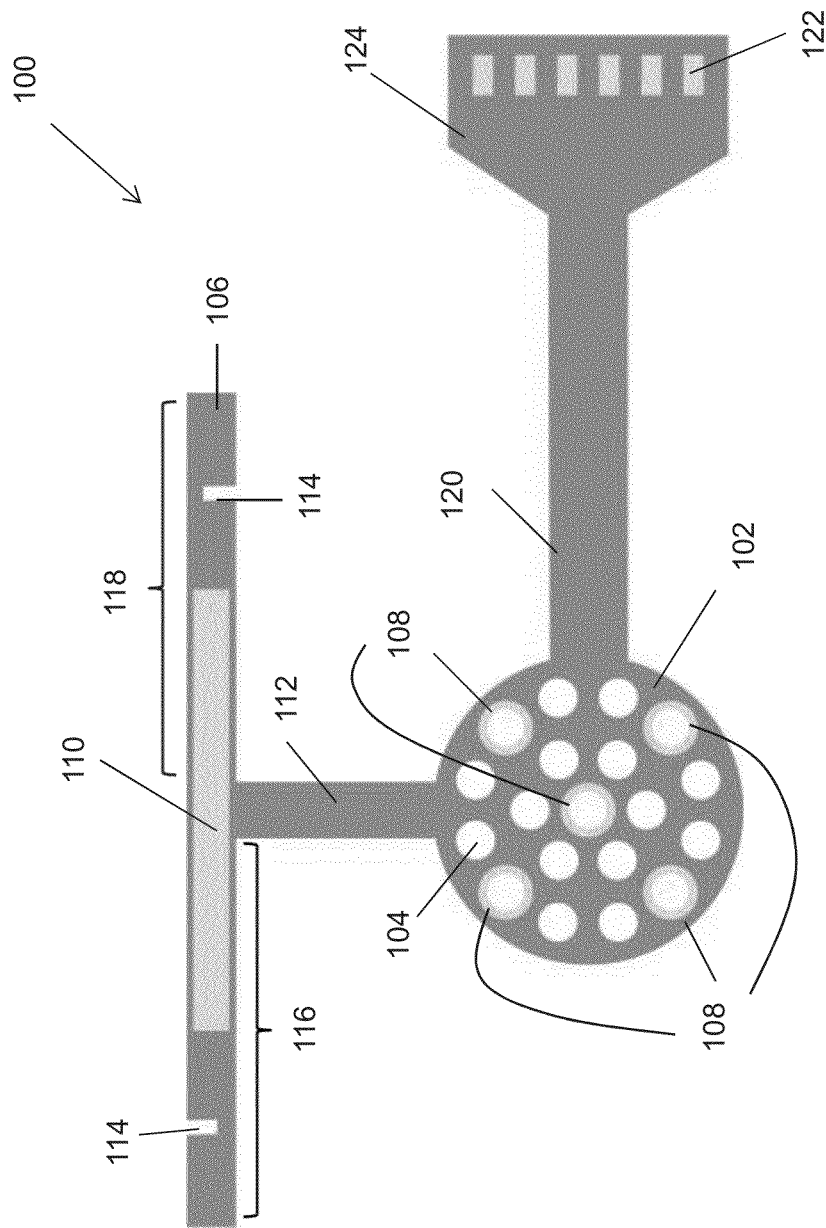
FIG. 1 shows a top view of a nerve stump interface in accordance to a preferred embodiment.

The following provides sample, but not exhaustive, definitions for expressions used throughout various embodiments disclosed herein.

The term "nerve stump interface" may mean a device which is to be used at a portion of a nerve cell. The device may be used to promote axonal regeneration, such as when the nerve cell is injured.

The term "sieve" may mean a substrate including a plurality of through-holes, ports, or sieve holes, through which regeneration of nerve filaments (neuritis) takes place after the implantation of the sieve in the region of the nerve stump.

The term "strip" may mean a length of material that extends from either side of the portion that attaches the length of material to the sieve. The length of material may be long enough so that the strip can be bent into the shape of a ring with the ends of the strip being adjacent to each other.

The terms "first electrode" and "second electrode" are electrical terminals that are wired to provide an open circuit connection, so that when they are powered by an energy source, a voltage gradient is created, thereby inducing an electric field between the first and second electrodes.

The term "securing element" may mean means provided on the strip to allow the strip to secure against itself, when the strip is bent to form a ring or loop shape. Such means include a notch cut into the strip.

The term "feeder" may mean a structure, integral with the sieve, upon which the first electrode and the second electrode are continued up to an external connector, by way of, for example, contact pads provided on the feeder.

DETAILED DESCRIPTION

In the following description, various embodiments are described with reference to the drawings, where like reference characters generally refer to the same parts throughout the different views.

Various embodiments are based on an operating principle that an electric field can guide the direction and hasten axonal regeneration in a peripheral nervous system. Various embodiments use a sieve-like electrode structure with an anode ring structure to create an electric field for promoting and guiding the axonal regeneration. To efficiently make the anode ring structure and integrate the device into a guidance tube, a notch design with biodegradable glue is used. Biological tissue is embedded into the guidance tube and will serve as termination substance for axonal regeneration from a proximal nerve stump. The device can be integrated with customized electronics (packaged in a hermitic container), wireless communication and power links to have a fully implantable PNI (peripheral nerve interface) for motorized limb prosthetic applications.

FIG. 1 shows a top view of a nerve stump interface 100 for generating an electric field for promoting and guiding axonal regeneration, in accordance to a preferred embodiment. The nerve stump interface 100 is shown in its pre-completed form, i.e. before the necessary steps are taken to have the nerve stump interface 100 arranged in its in-use configuration (see FIG. 3) to promote axonal regeneration. Accordingly, the nerve stump interface 100 has peripheral nervous system (PNS) applications.

The nerve stump interface 100 comprises a sieve 102 comprising a plurality of holes 104. The holes 104 of the sieve 102 provide through-holes or ports through which the regeneration of nerve filaments (neuritis) takes place after the implantation of the sieve 102 in the region of a nerve stump (not shown). A first electrode 108 is provided at one of the plurality of holes 104.

A strip 106 is coupled to the sieve 102. A second electrode 110 is provided on the strip 106. The strip 106 is arranged to space (for example, by a spacer 112) the second electrode 110 from the first electrode 108. The spacer 112 and the strip 106 form a "T" shaped structure that is attached to the sieve 102.

The spacer 112 ensures that the first electrode 108 and the second electrode 110 have an electrical open circuit, which facilitates the first electrode 108 and the second electrode 110 to generate an electric field, when there is a potential difference between the first electrode 108 and the second electrode 110. The electric field that will be generated between the first electrode 108 and the second electrode 110 will assist in the regeneration of the nerve filaments occurring at the holes 104 of the sieve 102.

At least one securing element 114 is provided on a side 116 of the strip 106 to allow that side 116 of the strip 106 to affix against an opposite side 118 of the strip 106. As shown in FIG. 1, a further securing element 114 is provided at the opposite side 118 of the strip 106. While FIG. 1 shows that there are two securing elements 114, it will be appreciated that when the strip 106 is rolled into a ring shaped structure (see FIGS. 4A and 4B), only one securing element 114 is needed to hold the opposite sides (116 and 118) of the strip 106 together and maintain the ring shaped structure.

The two securing elements 114 are provided in the vicinity of opposite ends of the strip 106. In the preferred embodiment of FIG. 1, the securing element 114 is a notch which is cut into the strip 106. Each notch is cut in a manner so that their respective openings face one another when the strip 106 is rolled to form a ring shaped structure (see FIG. 4B). When the notches engage one another, they are able to sit within one another to form a snug fit.

While only a single first electrode 108 is required, the preferred embodiment of FIG. 1 has a total of five of the first electrodes 108, each provided on one of the holes 104. The number of first electrodes 108 depends on the respective application and may vary up to a number corresponding to the number of holes 104.

Each first electrode 108 may be disposed along a circumference of the respective hole 104. The first electrode 108 on the substrate of the sieve 102 is preferably configured as a ring electrode around the respective hole 104, as shown in FIG. 1.

The first electrodes 108 may, of course, also be disposed in another form, e.g. as punctiform electrodes between the holes. Another possible form for the first electrodes 108 is shown in FIGS. 2A and 2B.

Figure 2:
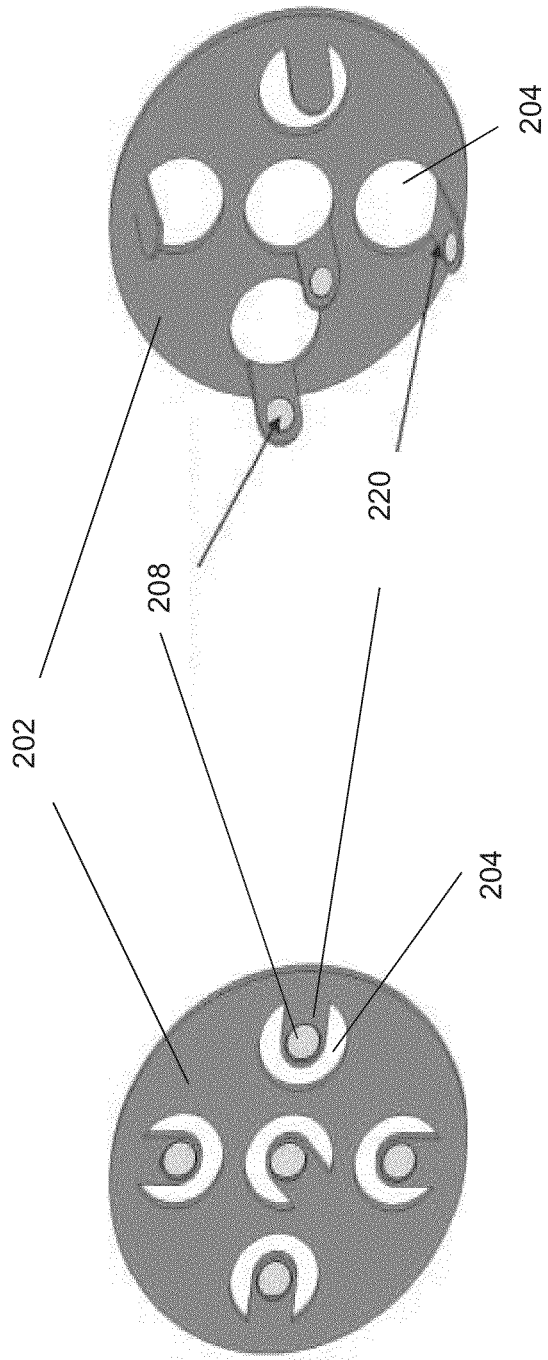
FIGS. 2A and 2B show possible form for electrodes used in the nerve stump interface shown in FIG. 1.

For the purpose of simplicity, FIGS. 2A and 2B show only a sieve 202 of a nerve stump interface according to another embodiment. The sieve 202 of FIGS. 2A and 2B is similar to the sieve 102 of FIG. 1 in that the sieve 202 comprises a substrate that has a plurality of holes 204. The holes 204 of the sieve 202 provide through-holes or ports through which the regeneration of nerve filaments (neuritis) takes place after the implantation of the sieve 202 in the region of a nerve stump (not shown). In this other embodiment of the nerve stump interface, a first electrode 208 is provided at one of the plurality of holes 204 by being provided on a protrusion 220 that extends from a portion of a circumference of the plurality of holes 204. FIG. 2A shows the protrusions 220 being flush with the sieve 202 surface. FIG. 2B shows the protrusions 220 being folded from their flush position of FIG. 2A to extend from the sieve 202 surface. The first electrodes 208 of FIGS. 2A and 2B are solid circle electrode (compared to the ring electrode structure of the first electrodes 108 of FIG. 1) that can increase contact area with nerve here axonal regeneration is to occur.

Returning to FIG. 1, the second electrode 110 has a rectangular configuration, in contrast to the solid circle or ring configurations of the first electrode 108. The second electrode may be used as reference electrode for the neural recording. The nerve stump interface 100 comprises a feeder 120 that extends from the sieve 102. When fully assembled (see FIG. 3), the feeder 102 provides the necessary wiring (not shown for the purpose of simplicity) for connection of the first electrode 108 and the second electrode 110 to, for example, a feed-through 329 in a hermitic container 328 (see FIG. 3) to power the first and second electrodes 108 and 110. The feed-through 329 comprises one or more contact pads. A plurality of contact pads 122 is provided at an end 124 of the feeder 120 that is opposite to the sieve 102. Each contact pad 122 is coupled to the first electrode 108 or the second electrode 110 by a respective conductor (not shown). Thus, for a total of six contact pads 122 shown in FIG. 1, the nerve stump interface 100 may have five first electrodes 108 and one single second electrode 110.

Figure 3:
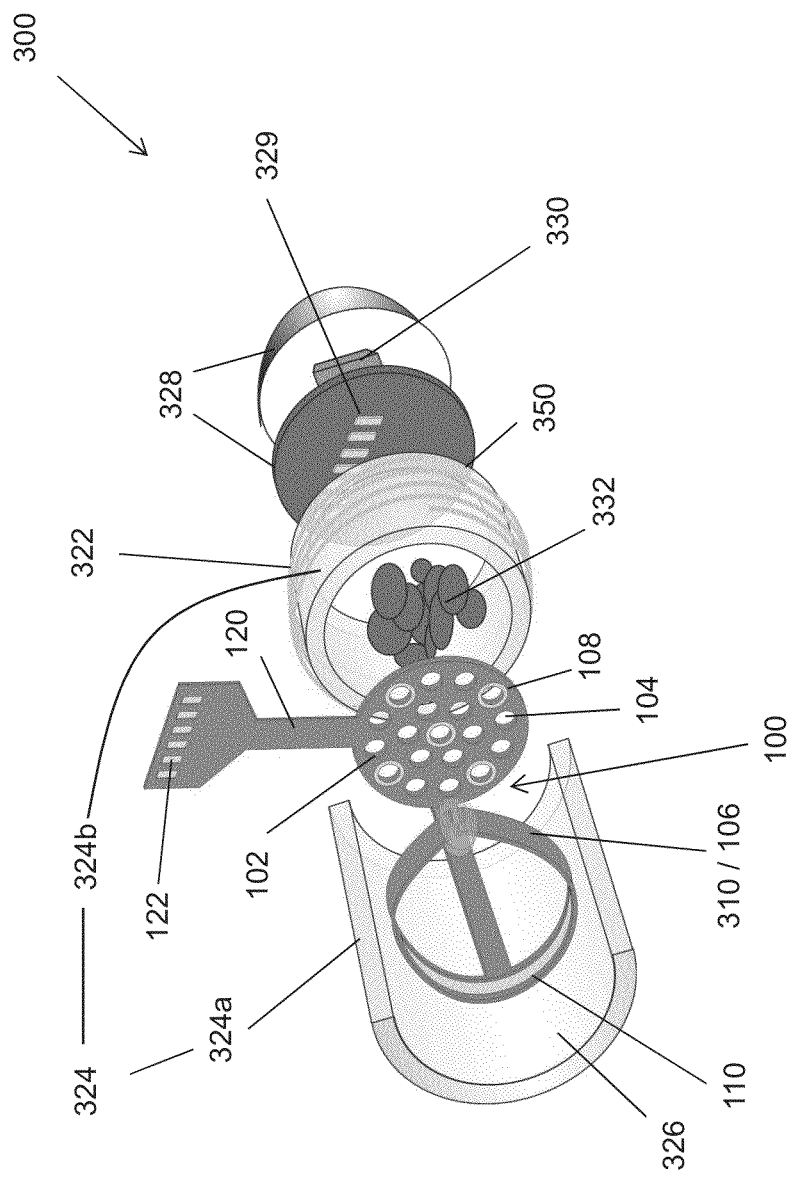
FIG. 3 shows an exploded view of an electric field assisted axonal regeneration system in accordance with an embodiment of the invention.

FIG. 3 shows an exploded view of an electric field assisted axonal regeneration system 300 in accordance with an embodiment of the invention. The electric field assisted axonal regeneration system 300 incorporates the nerve stump interface 100 of FIG. 1.

In more detail, the electric field assisted axonal regeneration system 300 comprises a guidance tube 324 with an open end 326. FIG. 3 shows that the guidance tube 324 is provided as two separate parts 324a and 324b, with the two separate parts joined together by, for example, silicone glue or plasma etch to hold the nerve stump interface 100 in position. However, it is also possible to mould the guidance tube 324 over the nerve stump interface 100 or provide the guidance tube 324 as a single piece with a slit that allows the nerve stump interface 100 to be introduced into the guidance tube 324 with the slit being subsequently sealed by, for example, silicone glue.

The sieve 102 has already been described above with reference to FIG. 1, in that the sieve 102 comprises a plurality of holes 104. In its in-use configuration, the sieve 102 is disposed in a perpendicular orientation within the guidance tube 324, so that the plurality of holes 104 faces the open end 326 of the guidance tube 324. Further, the strip 106 coupled to the sieve 102 is rolled to form a generally ring shaped structure 310 having an orientation that is generally parallel to the sieve 102.

As described above, the first electrode 108 is provided at one of the plurality of holes 104. A second electrode 110 is provided on the strip 106, the strip 106 being arranged to space the second electrode 110 from the first electrode 108, where the first electrode 108 and the second electrode 110 are for generating the electric field.

With the strip 106 rolled into the ring shaped structure 310, the second electrode 110 also acquires a ring shape. By providing a potential difference between the first electrode 108 and the second electrode 110, the ring shaped second electrode 110 provides a voltage gradient that is created that forms the electric field directed from the second electrode 110 to the first electrode 108. This promotes and guides axon regeneration towards the holes 104. As the regenerated axon approaches the holes 104, the electric field is concentrated around the second electrode 110 and passes through the holes 104.

When incorporated into the guidance tube 324, the feeder 120 extends from the sieve 102 to protrude from an exterior surface of the guidance tube 324, for instance a side wall of the fully assembled guidance tube 324. This has the effect of the plurality of contact pads 122 being provided at a portion of the feeder 120 that protrudes from the exterior surface of the guidance tube 324. As mentioned above, each contact pad 122 is coupled to the first electrode 108 or the second electrode 110 by a respective conductor (not shown for the purpose of simplicity).

An inductor 322 is disposed along an exterior surface of the guidance tube 324. FIG. 3 shows the inductor 322 being placed between an end 350 of the guidance tube 324 that is opposite to its open end 326 and the protruding feeder 120. In another embodiment, the inductor 322 may be placed at any other portion of the exterior surface of the guidance tube 324. Each terminal of the inductor 322 is connected to one of the contact pads provided at the feed-through 329 of a hermetic container 328 (see FIG. 3). As earlier mentioned, the first electrode 108 and the second electrode 110 are powered by being connected to the contact pads provided at the feed-through 329. In the embodiment shown in FIG. 3, the inductor 322 is an antenna coil.

The electric field assisted axonal regeneration system 300 further comprises nerve growth termination substance 332 disposed within the guidance tube 324. The nerve growth termination substance 332 is located adjacent to a surface of the sieve 102 that is opposite to the ring shaped structure 310. The nerve growth termination substance 332 may be biological tissue embedded in the guidance tube 324 and serves as termination substance for axonal regeneration from proximal nerve stump (not shown).

A hermitic container 328 is located at the end 350 of the guidance tube 324 opposite to its open end 326. The hermitic container 328 is used to package electronics 330 that comprise processing circuitry. This processing circuitry provides functions such as power management, voltage generation (i.e. for inducing the electric field created by the first electrode 108 and the second electrode 110), neural signal recording and wireless communication with any external device, such as a base station that monitors the status of the electric field assisted axonal regeneration system 300.

The first electrode 108 may be disposed along a circumference of the plurality of holes 104 formed in the sieve 102. As shown in FIG. 3, the first electrode 108 may be realized using ring electrodes. However, with cross-reference to FIG.

2B, the first electrode 208 may be provided on a protrusion 220 that extends towards the ring shaped structure 310.

The nerve stump interface 100 may be made from a polymer-metal-polymer sandwich structure using a standard micro-fabrication process. A sieve electrode may be used for the sieve 102, but with an additional "T" shaped structure that is used for the strip 106 having the second electrode 110 that forms an anode ring structure, as shown in FIG. 3. Also, as the nerve stump interface 100 is made from flexible polymer material, protruding electrode structures can be realized for the first electrode 208, as described above with respect to FIGS. 2A and 2B. The protrusions 220 are folded from their original flush position of FIG. 2A to an appropriate shape (see FIG. 2B), such as extending towards the ring shaped structure 310. Further, the use of a solid circle electrode (rather than a ring electrode) may increase contact area with nerve.

With reference to FIG. 1, two notches are provided in the "T" shaped structure of the spacer 112 and the strip 106 that facilitates an efficient electrode-tube assembly process. A method to assemble the electric field assisted axonal regeneration system 300 of FIG. 3 is described with reference to FIGS. 1 and 4A to 4D.

As shown in FIG. 1, a nerve stump interface 100 is provided. The nerve stump interface 100 comprises a sieve 102 comprising a plurality of holes 104. A strip 106 is coupled to the sieve 102. A first electrode 108 is provided at one of the plurality of holes 104 and a second electrode 110 is provided on the strip 106. The strip 106 is arranged to space the second electrode 110 from the first electrode 108. The first electrode 108 and the second electrode 110 are for generating the electric field. A securing element 114 is provided in the vicinity of each opposite end of the strip 106.

Figure 4D:
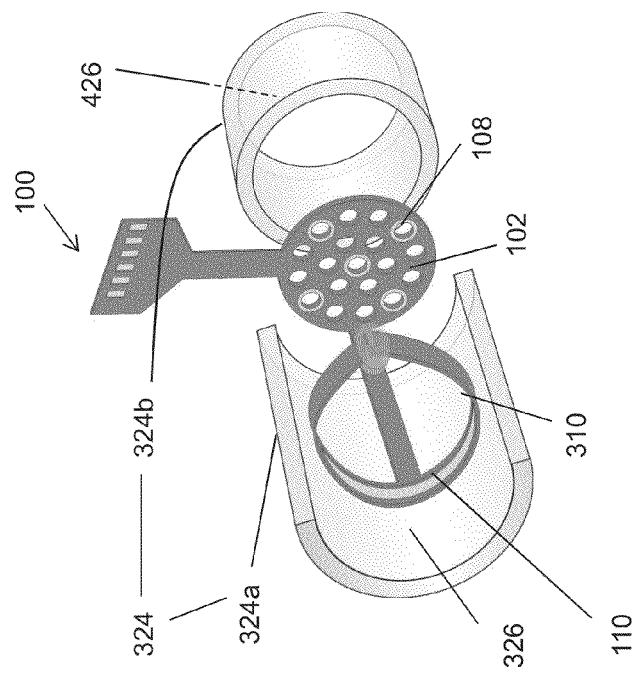
FIGS. 4A to 4D show a method to assemble the electric field assisted axonal regeneration system shown in FIG. 3.
Figure 4A:
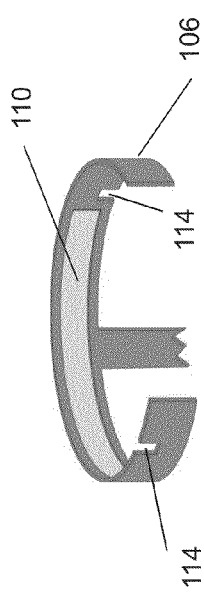
Figure 4B:
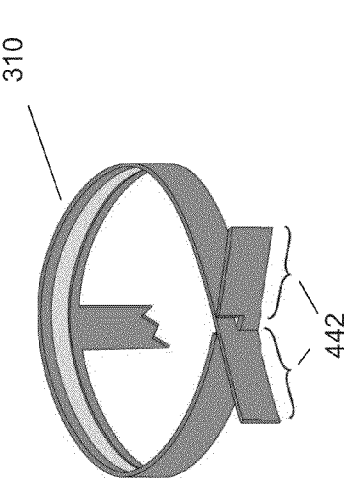
Figure 4C:
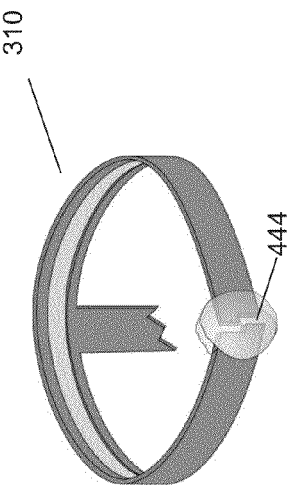

For the steps illustrated in FIGS. 4A to 4C, only a portion of the nerve stump interface 100 is shown, specifically the strip 106 coupled to the sieve 102, with the second electrode 110 thereon.

As shown in FIGS. 4A and 4B, the strip 106 is rolled to form a ring shaped structure 310 by having the securing element 114 at each opposite end engage one another. With notches used for the securing element 114, a simple assembly process is achieved that allows integration of the first electrode 108 and the second electrode 110 into any guidance tube (see FIG. 4D). The ring shaped structure 310 is then immobilized (using, for example but not limited to, biodegradable glue 444). In FIG. 4C, excess 442 (refer FIG. 4B) from the opposite ends of the strip 106 that extend from the engaged securing elements 114 is removed.

Either the ring shaped structure 310 or the sieve 102 is folded to be parallel to each other. The ring shaped structure 310 is then inserted within a guidance tube 324a, as shown in FIG. 4D.

For the steps shown in FIGS. 4A and 4B, the "T" shaped structure of the strip 106 can be rolled up by a pair of tweezers gripping the portion of the strip 106 that is between the securing element 114 and the respective end of the strip 106. This portion of the strip 106 provides a 'tweezers handle'. The temporary affixation provided by the notches of the engaged securing elements 114 is further strengthened by using biodegradable glue 444 such as PEG (polyethylene glycol) to immobilize the ring shaped structure 310 formed by rolling the strip 106, as shown in FIG. 4C. After the immobilization, the dummy 'tweezers handle' region can be removed, i.e. the excess 442 from the opposite ends of the strip 106 is severed. Either the ring shaped structure 310 or the sieve 102 is folded at an angle of 90°, as shown in FIG. 4D. The nerve stump interface 100 is then introduced into one end of a guidance tube 324a. Another guidance tube 324b is then used to secure the nerve stump interface 100 in place in the resulting guidance tube 324. The radius of the ring shaped structure 310 having the anode electrode (i.e. the second electrode 110) is slightly smaller than that of the guidance tube 324 to allow an efficient insertion process. The two guidance tubes 324a and 324b are secured together by plasma etch or silicone glue.

The first electrode 108 may be disposed along a circumference of the plurality of holes 104 formed in the sieve 102. As shown in FIG. 3, the first electrode 108 may be realized using ring electrodes. However, with cross-reference to FIG. 2B, the first electrode 208 may be provided on a protrusion 220 that extends towards the ring shaped structure 310.

The ring shaped structure 310 may be secured to an inner wall of the guidance tube 324. This securement may be done using silicone glue or via plasma etch. With reference to FIG. 3, nerve growth termination substance 332 can then be introduced. An open end 426 of the guidance tube 324 is then sealed with a hermetic container 328, so that an opposite end 326 of the guidance tube 324, adjacent to the ring shaped structure 310, remains open.

FIGS. 5A to 5E show an exemplary process to fabricate the nerve stump interface 100 as shown in FIG. 1. The exemplary process is further elaborated below, with reference to the nerve stump interface 100 shown in FIG. 1.

Figure 5D:
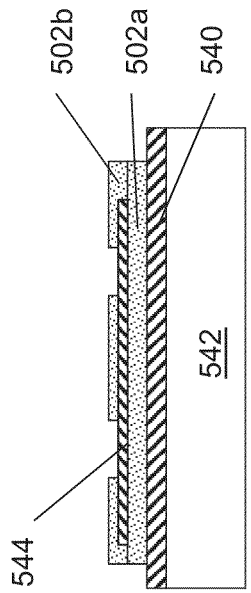
FIGS. 5A to 5E show an exemplary process to fabricate the nerve stump interface shown in FIG. 1.
Figure 5E:
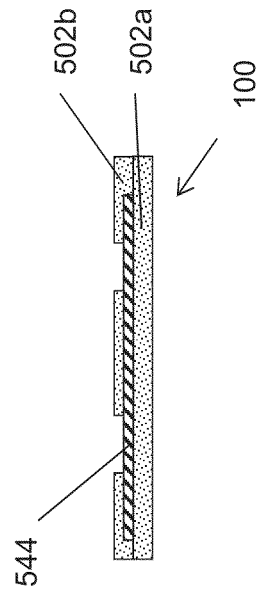
Figure 5A:
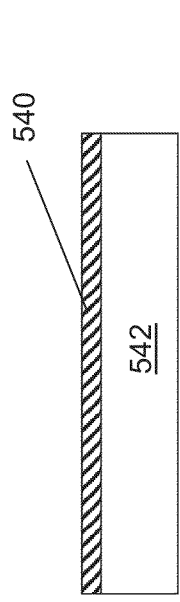
Figure 5B:
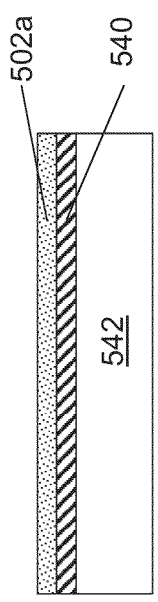

As shown in FIG. 5A, a sacrificial layer 540 (comprising, for example, aluminum) is deposited over a starting substrate 542 (comprising, for example, silicon). In FIG. 5B, a base layer 502a is deposited over the sacrificial layer 540 and cured. The base layer 502a may comprise, for example, polyimide is used as a substrate for the sieve 102, the spacer 112, the strip 106 and the feeder 120.

Figure 5C:
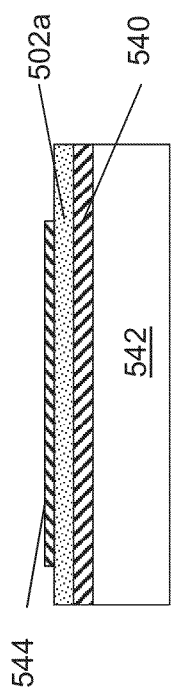

In FIG. 5C, a metal layer arrangement 544 is deposited onto the base layer 502a. The metal layer arrangement 544 is patterned to form the first electrode 108 and the second electrode 110. The metal layer arrangement 544 may comprise three layers with each fabricated from a metal such as titanium and gold. In one exemplary sequence of fabricating the metal layer arrangement 544, a Ti layer is first deposited, followed by a Au layer and finally an additional Ti layer on the Au layer.

In FIG. 5D, a top layer 502b is deposited over the base layer 502a and the metal layer arrangement 544. The top layer 502b is cured and patterned. The top layer 502b may comprise, for example, polyimide. Excess portions of both the base layer 502a and the top layer 502b on the electrical contact and electrodes are removed. The remaining top layer 502b and base layer 502a then form the sieve 102, the spacer 112, the strip 106 and the feeder 120. In FIG. 5E, the sacrificial layer 540 is dissolved, so as to release the nerve stump interface 100.

A nerve stump interface and an electric field assisted axonal regeneration system, both in accordance with an embodiment of the invention, provide MEMS (microelectromechanical systems) based sieve-type electrode with an anode ring structure. With reference to FIGS. 4A to 4D, the nerve stump interface may be realized from micromachining existing flexible sieve electrodes to monolithically integrate additional modules that facilitate electric field generation to promote axonal regeneration. There are several advantages over existing approaches. For instance, the nerve stump interface does not significantly increase the mass or size of standard sieve electrodes. Further, as described with reference to FIGS. 4A to 4D, a simple process is used to fabricate an electric field assisted axonal regeneration system, which reduces fabrication cost. In addition, by using an inductor to power the electrodes that guide and promote axonal regeneration, a wireless power supply is provided that is in turn powered by external means. Axonal regeneration is thus not constrained by a battery energy level, whereby if an internal battery is used as a power source, the battery would eventually deplete. The electric field assisted axonal regeneration system also provides a single-ended interface for peripheral nervous system (PNS) applications.

Figure 6A:
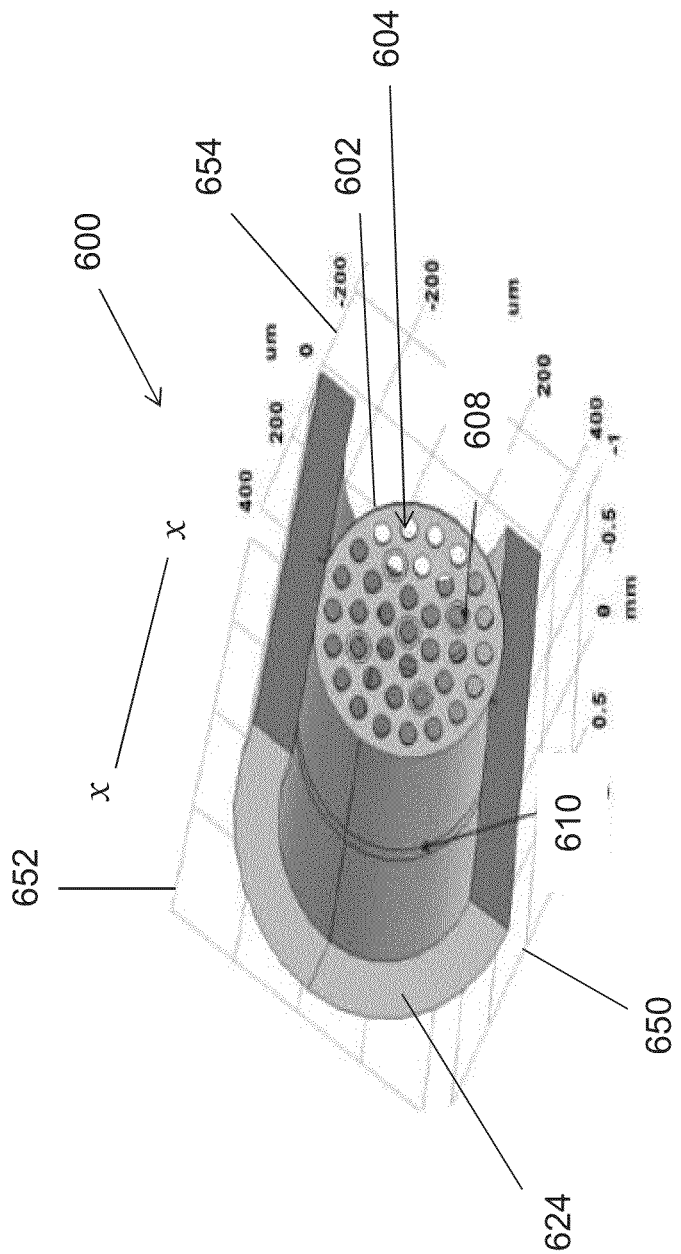
FIG. 6A shows a cross sectional view of a computer simulated electric field assisted axonal regeneration system built in accordance to the one shown in FIG. 3.

FIG. 6A shows a cross sectional view of a computer simulated electric field assisted axonal regeneration system 600, which is similar to the electric field assisted axonal regeneration system 300 shown in FIG. 3. For the purposes of simplicity, only a sieve 602, an anode ring electrode 610 and a guidance tube 624 of the simulated electric field assisted axonal regeneration system 600 is shown. The sieve 602 has a plurality of holes 604, with several having an electrode 608 thereupon. FIG. 6A provides an exemplary scale to which an electric field assisted axonal regeneration system, according to various embodiments, may be built, as shown in the reference planes 650, 652 and 654.

Figure 6D:
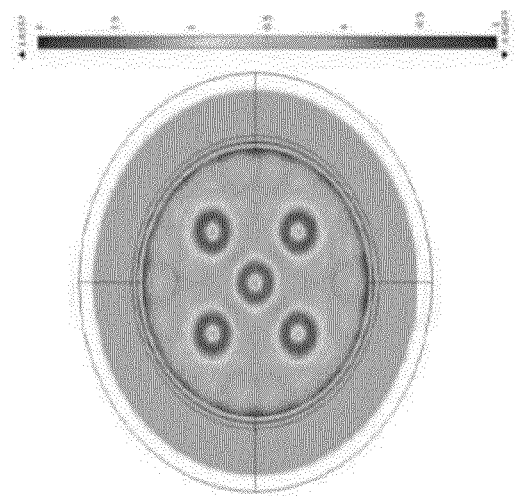
FIGS. 6B to 6D show simulation results of an electric field distribution for this computer simulated electric field assisted axonal regeneration system.
Figure 6B:
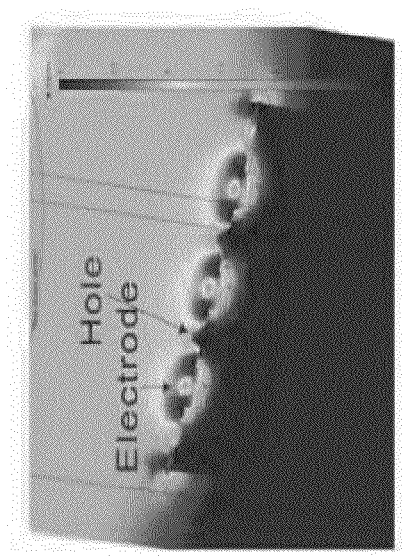
Figure 6C:
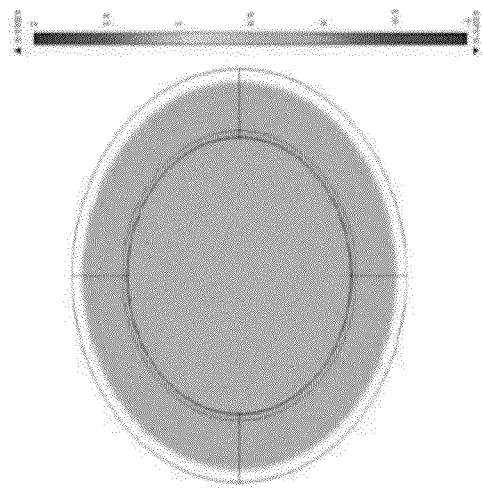

FIGS. 6B to 6D show simulation results indicating electric field distribution at three positions along the guidance tube 624 by injecting a current from the anode ring electrode 610 to the electrodes 608. FIG. 6B shows electric field distribution along a cross-slice of the guidance tube 624 (i.e. along a direction X-X shown in FIG. 6A). FIG. 6C shows electric field distribution at the middle between the anode ring electrode 610 and the electrodes 608. FIG. 6D shows electric field distribution in a 10 μm vicinity of the electrodes 608. The above electric field distributions within the electric field assisted axonal regeneration system 600 are simulated by solving the quasi-static Maxwell's equation ($\sigma\nabla^2 V = -\nabla \cdot \vec{J}$) using commercial finite element analysis software (for example, "COMSOL4.2"). The stimulation results show that an injection of current with a density of 100 μA/cm$^2$ from the anode ring electrode 610 to the electrodes 608 creates a steady electric field with a voltage gradient of approximately 10 mV/mm between the anode ring electrode 610 and the electrodes 608, as shown in FIGS. 6B and 6C, to promote nerve regeneration. It will be appreciated that the current injection may be provided by an inductor present in the electric field assisted axonal regeneration system 600 (which is not shown in FIG. 6A).

Approaching the electrodes 608, the electrical field concentrates around the electrodes 608, as shown in FIGS. 6B and 6D. Given that axons prefer to grow towards a cathode, hence the axons will be guided by the electrical field to grow pass through the electrodes 608, rather than other regions.

FIG. 7 shows a table of possible materials that can be used for the various components of the electric field assisted axonal regeneration system 300 shown in FIG. 3.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

What is claimed is:

1. A nerve stump interface for generating an electric field for promoting and guiding axonal regeneration, the nerve stump interface comprising
 a sieve comprising a plurality of holes;
 a strip coupled to the sieve;
 a first electrode provided at one of the plurality of holes and a second electrode provided on the strip, the strip being arranged to space the second electrode from the first electrode, the first electrode and the second electrode for generating the electric field; and
 at least one securing element provided on a side of the strip to allow that side of the strip to affix against an opposite side of the strip.

2. A nerve stump interface according to claim 1, wherein a further securing element is provided at the opposite side of the strip.

3. A nerve stump interface according to claim 2, wherein the two securing elements are provided in the vicinity of opposite ends of the strip.

4. A nerve stump interface according to claim 1, wherein the securing element is a notch.

5. A nerve stump interface according to claim 1, wherein the first electrode is disposed along a circumference of the plurality of holes.

6. A nerve stump interface according to claim 1, wherein the first electrode is provided on a protrusion that extends from a portion of a circumference of the plurality of holes.

7. A nerve stump interface according to claim 1, further comprising a feeder extending from the sieve; and
 a plurality of contact pads provided at an end of the feeder opposite to the sieve, wherein each contact pad is coupled to the first electrode or the second electrode by a respective conductor.

8. An electric field assisted axonal regeneration system comprising:
 a guidance tube with an open end;
 a sieve comprising a plurality of holes, the sieve disposed in a perpendicular orientation within the guidance tube, so that the plurality of holes faces the open end of the guidance tube;
 a strip coupled to the sieve and rolled to form a generally ring shaped structure, the ring shaped structure having an orientation that is generally parallel to the sieve;
 a first electrode provided at one of the plurality of holes; and
 a second electrode provided on the strip, the strip being arranged to space the second electrode from the first electrode, the first electrode and the second electrode for generating the electric field.

9. An electric field assisted axonal regeneration system according to claim 8, further comprising
 a feeder extending from the sieve to protrude from an exterior surface of the guidance tube; and
 a plurality of contact pads provided at a portion of the feeder that protrudes from the exterior surface of the guidance tube, wherein each contact pad is coupled to the first electrode or the second electrode by a respective conductor.

10. An electric field assisted axonal regeneration system according to claim 8, further comprising nerve growth termination substance disposed within the guidance tube, the nerve growth termination substance being located adjacent to a surface of the sieve opposite to the ring shaped structure.

11. An electric field assisted axonal regeneration system according to claim 8, further comprising a hermitic container located at the end of the guidance tube opposite to its open end; and processing circuitry for the electric field assisted axonal regeneration system, the processing circuitry being packaged in the hermitic container.

12. An electric field assisted axonal regeneration system according to claim 11, further comprising an inductor coupled to the processing circuitry, the inductor being disposed along an exterior surface of the guidance tube.

13. An electric field assisted axonal regeneration system according to claim 8, wherein the first electrode is disposed along a circumference of the plurality of holes.

14. An electric field assisted axonal regeneration system according to claim 8, wherein the first electrode is provided on a protrusion that extends towards the ring shaped structure.

15. A method for assembling an electric field assisted axonal regeneration system, the method comprising:
- providing a nerve stump interface comprising:
  - a sieve comprising a plurality of holes;
  - a strip coupled to the sieve;
  - a first electrode provided at one of the plurality of holes and a second electrode provided on the strip, the strip being arranged to space the second electrode from the first electrode, the first electrode and the second electrode for generating the electric field; and
  - a securing element provided in the vicinity of each opposite end of the strip;
- rolling the strip to form a ring shaped structure by having the securing element at each opposite end engage one another;
- immobilizing the ring shaped structure;
- removing excess from the opposite ends of the strip that extend from the engaged securing elements;
- folding either the ring shaped structure or the sieve to be parallel to each other; and
- inserting the ring shaped structure within a guidance tube.

16. A method for assembling an electric field assisted axonal regeneration system according to claim 15, wherein the first electrode is disposed along a circumference of the plurality of holes.

17. A method for assembling an electric field assisted axonal regeneration system according to claim 15, wherein the first electrode is provided on a protrusion that extends towards the ring shaped structure.

18. A method for assembling an electric field assisted axonal regeneration system according to claim 15, wherein the ring shaped structure is immobilized using biodegradable glue.

19. A method for assembling an electric field assisted axonal regeneration system according to claim 15, the method further comprising securing the ring shaped structure to an inner wall of the guidance tube.

20. A method for assembling an electric field assisted axonal regeneration system according to claim 15, the method further comprising sealing an open end of the guidance tube with a hermetic container, so that an opposite end of the guidance tube, adjacent to the ring shaped structure, remains open.

\* \* \* \* \*

UNITED STATES PATENT AND TRADEMARK OFFICE
CERTIFICATE OF CORRECTION

PATENT NO. : 9,199,073 B2  Page 1 of 1
APPLICATION NO. : 14/093351
DATED : December 1, 2015
INVENTOR(S) : Tsang et al.

It is certified that error appears in the above-identified patent and that said Letters Patent is hereby corrected as shown below:

On the title page item [30], in column 1, line 1, delete "201208821" and insert --201208821-7--, therefor Signed and Sealed this
Twelfth Day of April, 2016

Michelle K. Lee
*Director of the United States Patent and Trademark Office*